United States Patent
Powell et al.

(10) Patent No.: US 7,488,939 B2
(45) Date of Patent: Feb. 10, 2009

(54) PROCESS MONITORING OF MOLDED CLOSURES

(75) Inventors: Mark A. Powell, Crawfordsville, IN (US); Michael E. Albertson, Crawfordsville, IN (US); Paul W. Robbins, Crawfordsville, IN (US)

(73) Assignee: Alcoa Closure Systems International, Inc., Crawfordsville, IN (US)

( * ) Notice: Subject to any disclaimer, the term of this patent is extended or adjusted under 35 U.S.C. 154(b) by 770 days.

(21) Appl. No.: 11/118,633

(22) Filed: Apr. 29, 2005

(65) Prior Publication Data

US 2006/0244952 A1    Nov. 2, 2006

(51) Int. Cl.
G01J 5/00 (2006.01)
B28B 1/24 (2006.01)

(52) U.S. Cl. .............................. 250/339.04; 250/339.06; 425/170; 264/40.1

(58) Field of Classification Search .................. 250/337, 250/338.1, 339.04, 339.06; 264/40.1; 425/169, 425/170
See application file for complete search history.

(56) References Cited

U.S. PATENT DOCUMENTS

| | | | |
|---|---|---|---|
| 3,910,737 A | 10/1975 | Shimada et al. ............. 425/140 |
| 4,187,267 A | 2/1980 | Fisher et al. ................ 264/40.1 |
| 4,963,302 A | 10/1990 | Heindl et al. ............... 264/40.4 |
| 5,384,079 A | 1/1995 | Bur et al. ........................ 264/21 |
| 5,591,385 A | 1/1997 | Arai et al. ................... 264/40.6 |
| 5,715,062 A | 2/1998 | Ota ............................. 356/376 |
| 5,766,538 A | 6/1998 | Kossman ..................... 264/407 |
| 6,494,706 B2 | 12/2002 | Tumlin et al. ............... 425/577 |
| 6,546,311 B2 | 4/2003 | Brown ......................... 700/200 |
| 6,592,354 B2 | 7/2003 | Kachnic et al. | |
| 6,810,303 B2 | 10/2004 | Sagae et al. | |
| 2002/0153624 A1 | 10/2002 | Tumlin et al. .............. 264/1.25 |
| 2003/0026865 A1 | 2/2003 | Tumlin et al. ............... 425/141 |
| 2003/0030160 A1 | 2/2003 | Tumlin et al. ................ 264/2.2 |

OTHER PUBLICATIONS

PCT/US06/15963—International Search Report and Written Opinion, Mar. 8, 2007, Alcoa Closure Systems International, Inc.

*Primary Examiner*—David P Porta
*Assistant Examiner*—Mark R Gaworecki
(74) *Attorney, Agent, or Firm*—Wood, Phillips, Katz Clark & Mortimer

(57) ABSTRACT

A method and apparatus is disclosed for inspection of molded closures that would measure specific parameters of the closure on an on-line basis as they are ejected from an associated compression molding apparatus. Measuring specific parameters of the closure on an on-line basis identifies problems with specific tool sets, sub-systems, and process settings of the molding apparatus, thus substantially reducing the amount of scrap that is produced.

28 Claims, 4 Drawing Sheets

PROCESS MONITORING OF MOLDED CLOSURES

FIELD OF THE INVENTION

The present invention generally relates to process monitoring of molded closures. In particular, the invention relates to an apparatus and method for monitoring molded closures after manufacture of the closures.

BACKGROUND OF THE INVENTION

A rotary compression molding apparatus is typically employed for the manufacture of molded plastic closures. A rotary turret carries multiple, vertically oriented tool assemblies which are rotated by the turret relative to upper and lower fixed cams. Rotary motion of the tooling relatively moves respective sets of upper and lower or, male and female, mold assemblies. As the turret rotates, a metered charge of molten plastic is placed into each open female mold, and the male and female molds relatively move to compress the molten plastic therebetween to form the closure. Liquid cooling within the tooling promotes rapid plastic solidification. The molding cycle is completed by relative movement of the tooling to open the mold cavity, and eject the molded closure.

Quality monitoring or inspection techniques employed after compression molding have necessarily resulted in a lag time between identification of molding problems and their correction. By one inspection technique, molded closures are sampled, and carefully measured. As a result of the time lag between identification of a problem and its correction, many unacceptable closures may be produced. It is also possible that poor quality closures can be manufactured between the times at which samples are taken. Additionally, the detection of a poor quality closure does not necessarily identify the specific problem that resulted in its formation, thus requiring secondary measurements and process experiments to determine the cause of the faults. Examples of secondary measurements and process experiments would be dimensional measurements obtained from a coordinate measuring machine or a caliper.

Another technique for inspecting molded closure parts employs a vision-based inspection system, which visually inspect either periodic closure samples, or 100% of the closures being molded. However, these systems have proven to be expensive to implement in connection with high speed production, which may entail hundreds of closures per minute. Such vision-based systems are sensitive to the background lighting of the room that the apparatus is in and process lighting angles. While the time lag between manufacturing and inspection is minimal, detection of poor quality closures does not give specific information regarding the cause of the problem.

An inspection or monitoring system is needed wherein measurement of molded closures can be effected on an on-line basis as they are ejected from an associated compression molding apparatus. The testing would be conducted in a fashion such that each individual closure can be associated with a particular one of the mold tooling sets of the molding apparatus. Problems associated with the specific tool set can thus be readily identified. Furthermore, by monitoring specific parameters, specific sub-systems and process settings of the molding apparatus could be modified. For example, temperature measurement of each closure correlates to dimensional shifts, quality shifts, and cooling system performance. Measurement of top panel thickness correlates directly to closure weight and final dimensions. Warpage indicators or the concavity of the closure top surface, correlate directly to cooling flow and plastic melt temperature.

Combinations of measurements' behavior would allow technicians to quickly diagnose a problem and point to a sub-system of the molder, or individual tool that would require maintenance or adjustment. Because the measurements would be variables, rather than attributes, they would lend themselves to control charting, and would indicate processes that were changing, thus giving early warning of changing processes and allowing maintenance and adjustment to be performed before scrap is produced. This would be in direct distinction from the previous methods, which are only triggered when scrap is produced.

The primary object of the present invention is to provide a method and apparatus for monitoring molded closures that would measure specific parameters of the closure so that problems with specific tool sets, sub-systems, and process settings of the molding apparatus could be identified, thus substantially reducing the amount of scrap that is produced.

SUMMARY OF THE INVENTION

The present invention is directed to an apparatus and method for monitoring molded plastic closures after manufacture of the closures. The method comprises passing the closures above an infrared sensor and measuring the temperature of the top panel of the closures, passing the closure above a first laser and measuring the concavity of the top panel, passing the closure under a second laser and measuring the location of the inside surface of the top panel, obtaining the thickness of the top panel by subtracting the concavity of the top panel from the location of the inside surface of the top panel, and approving or rejecting the closure. The infrared sensor measures the temperature of the top panel by emitting an infrared beam, preferably having a wavelength between about 8 to about 14 microns, onto the top panel surface and collecting the intensity of the beam reflectance from it. The first and second lasers measure the concavity and the location of the inside surface of the top panel by emitting a laser beam, preferably having a wavelength that is about 670 nanometers, onto the outside and inside surface of the top panel and collecting the distance between these surfaces and the laser face. The closures are approved or rejected by analyzing the measurements of the infrared sensor and the first and second lasers with a data acquisition control system that is connected to the infrared sensor and the first and second lasers. The measurements are then presented on a graphical user interface.

The apparatus comprises an aluminum coated platform having an aluminum-coated supporting structure and a pocketwheel having pockets, a closure feeding means for feeding the closure to the pocketwheel, and a closure receiving means for receiving the closure after the closure is discharged from the pocketwheel. The closure feeding means and closure receiving means are preferably also pocketwheels having pockets for holding the closures. The pockets for the closure feeding pocketwheel, pocketwheel, and closure receiving pocketwheel are preferably 30 mm in diameter. The pocketwheel is radially oriented from the closure feeding pocketwheel and the closure receiving pocketwheel is radially oriented from the pocketwheel and across from the closure feeding pocketwheel. The pocketwheel, closure feeding pocketwheel, and closure receiving pocketwheel are connected to the platform via coupling means, preferably gears that have a motor coupled to them and allow the gears to transfer motion to the pocketwheels. The closure feeding pocketwheel and the closure receiving pocketwheel move in a direction opposite the pocketwheel. In addition, the infrared sensor is coupled to the platform and the first and second lasers, respectively positioned below and above the platform, are coupled to the supporting structure.

In operation, the closure feeding pocketwheel accepts the closure from a molding apparatus and passes the closure to the pocketwheel. The pocketwheel passes the closure above the infrared sensor and the first laser and below the second laser, with the sensors and the lasers each measuring a parameter of the closure for approval or rejection. The pocketwheel passes the approved closures to the closure receiving pocketwheel, which clears these closures from the platform. The rejected closures are cleared from the platform by an airway situated on the side of the platform. The platform includes an aperture to receive the infrared beam from the infrared sensor and a slot to receive the laser beam from the first laser. The aperture is about a quarter inch in diameter and the slot is about an eighth inch in width and one inch in length. The closure feeding pocketwheel, preferably made of high density polyethylene, and the closure receiving pocketwheel, preferably made of coated aluminum, are about four and one-half inches in diameter. The pocketwheel, preferably made of coated aluminum, is about seven inches in diameter.

DETAILED DESCRIPTION OF PREFERRED EMBODIMENTS

Figure 1:
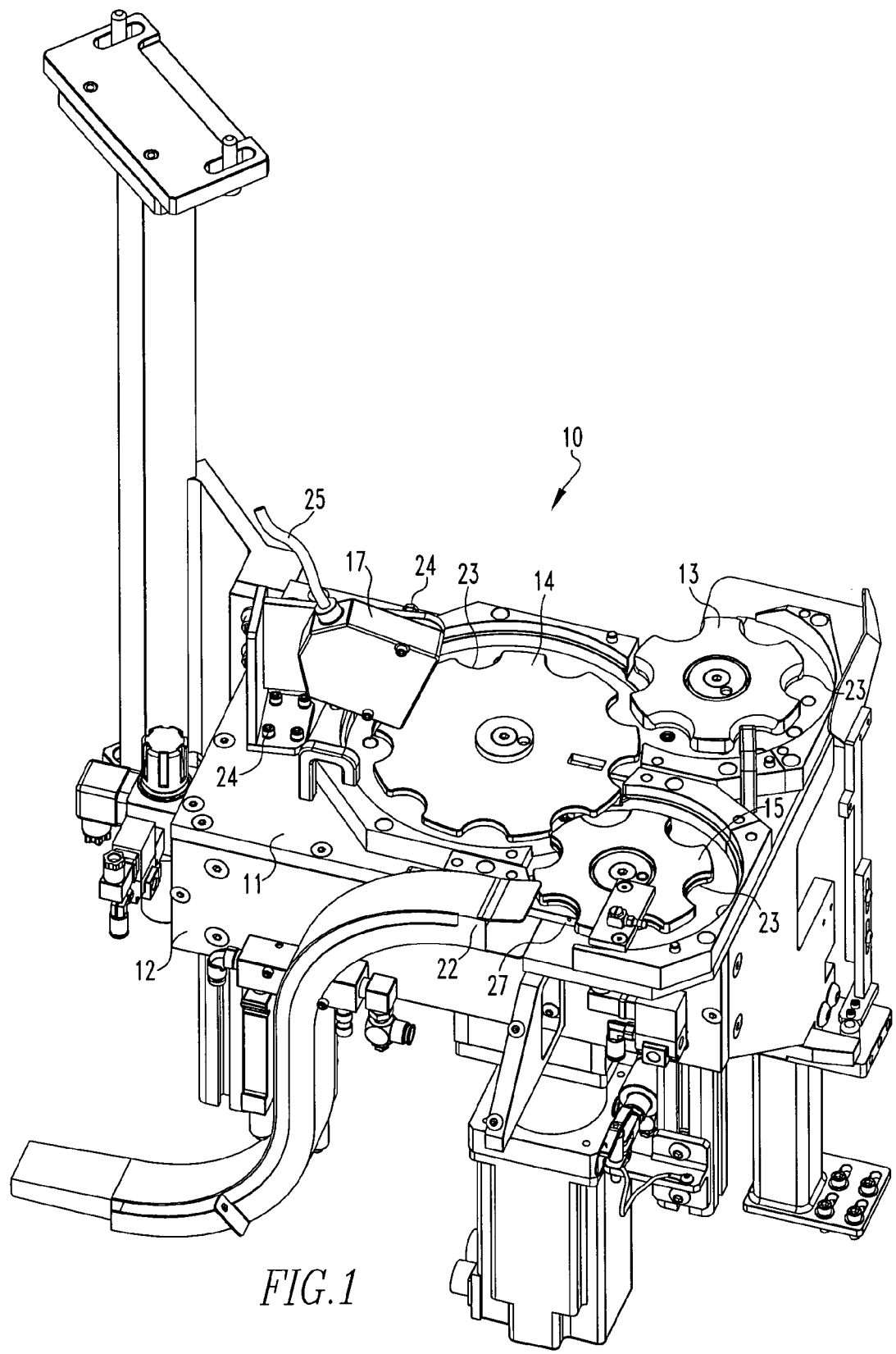
FIG. 1 is a perspective view of the closure monitor apparatus.

FIG. 1 shows a perspective view of the closure monitor apparatus 10 of the invention. The apparatus 10 comprises a platform 11 having a supporting structure 12 and a pocketwheel 14, a closure feeding means 13 for feeding the closure to the pocketwheel 14, and a closure receiving means 15 for receiving the closure after the closure is discharged from the pocketwheel 14, each of which are coupled to the platform 11. For the purposes of this preferred embodiment, the closure feeding means 13 and closure receiving means 15 each comprise a pocketwheel. However, other means that would properly feed and receive the closures to and from the pocketwheel 14, such as conveyor belts, could be used. The platform 11 and the supporting structure 12 are both made from metal, preferably coated aluminum. Together, the platform and supporting structure are about fifteen inches wide and ten inches high. The pocketwheels 13, 14, 15 each have pockets 23 for housing a closure during the monitoring process and are situated so that the pocketwheel 14 is radially oriented from the closure feeding pocketwheel 13 and the closure receiving pocketwheel 15 is radially oriented from the pocketwheel 14 and across from the closure feeding pocketwheel 13. The closure feeding pocketwheel and closure receiving pocketwheel 13,15 are about four and a half inches in diameter and the pocketwheel 14 is about seven inches in diameter. The pockets 23 for the pocketwheels 13, 14, 15 are about thirty millimeters in diameter. In addition, the closure feeding pocketwheel 13 comprises plastic, preferably high definition polyethylene, and the pocketwheel and closure receiving pocketwheel 14,15 comprise metal, preferably coated aluminum. Pocketwheels comprised of aluminum leave marks on the closure and therefore contaminate the closure. Therefore, the pocketwheel and closure receiving pocketwheel 14, 15 are comprised of coated aluminum to substantially reduce the number of marks left on the closure. As will be described below, during the monitoring process, the closure feeding pocketwheel 13 accepts a closure from a molding apparatus. During this time, the possibility exists for the closure feeding pocketwheel 13 and the molding apparatus to collide and cause damage to the tooling for the molding apparatus. If the closure feeding pocketwheel 13 is comprised of plastic, which is softer than other materials such as coated aluminum, then damage to the tooling will be substantially reduced.

Figure 3:
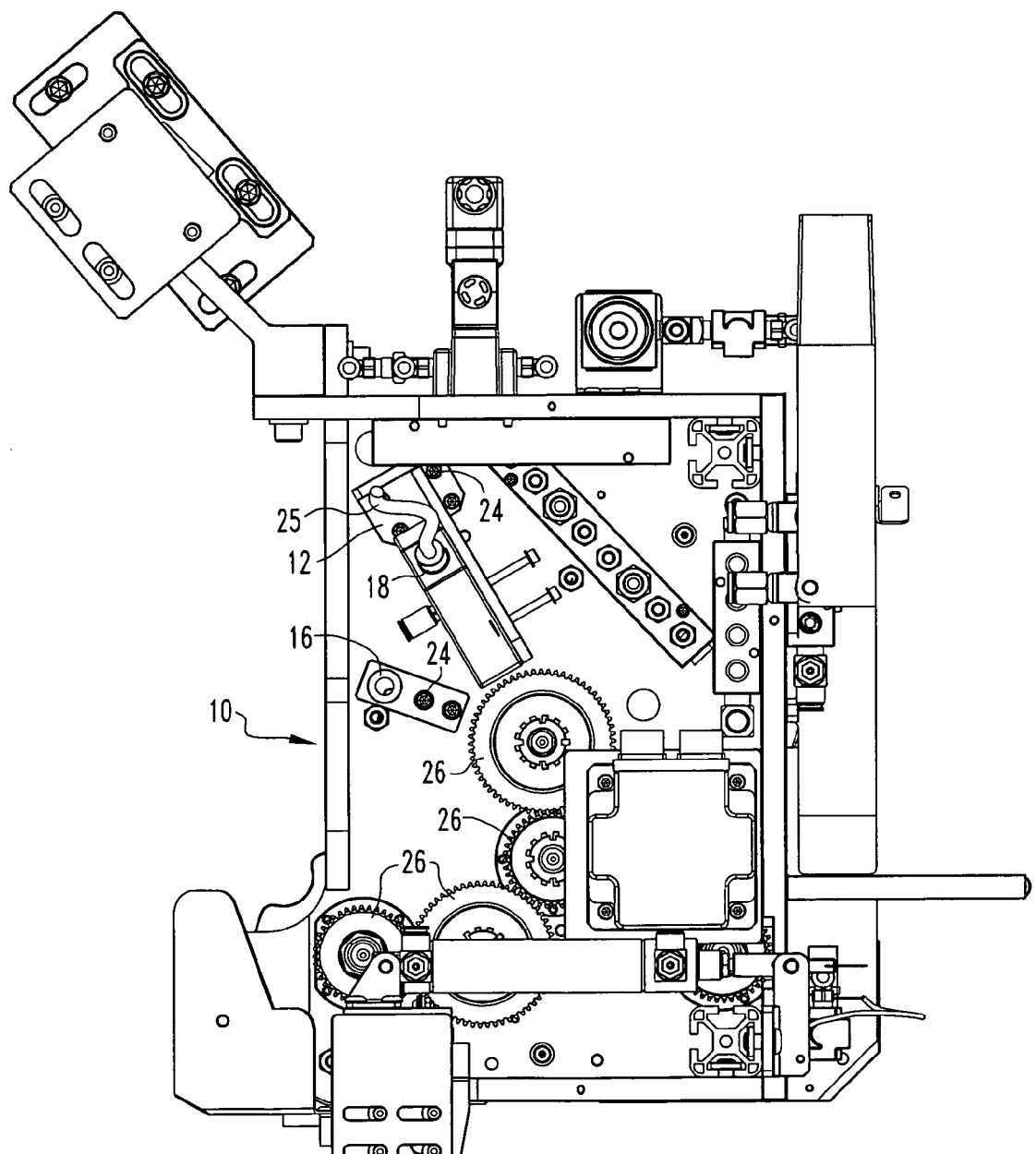
FIG. 3 is a bottom view of the closure monitor apparatus.
Figure 4:
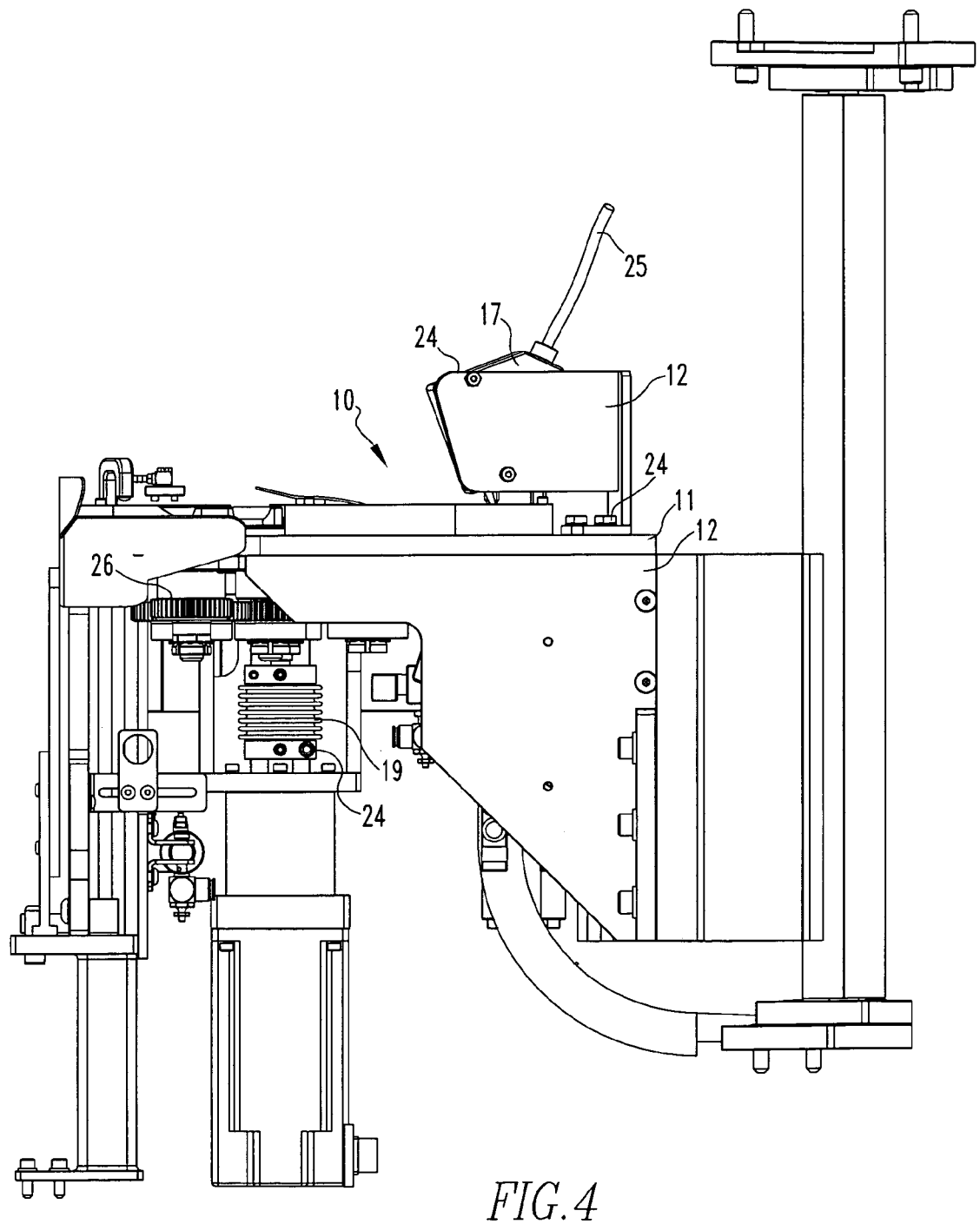
FIG. 4 is a back view of the closure monitor apparatus.

The apparatus 10 also comprises an infrared sensor (FIG. 3, 16) that is coupled to the platform 11, a first laser (FIG. 3, 18) that is coupled to the supporting structure 12 and situated below the platform 11 and under the pocketwheel 14, and a second laser 17 that is also coupled to the supporting structure 12 and situated above the pocketwheel 14. For the purposes of this invention, the infrared sensor (FIG. 3, 16) is preferably a high speed infrared sensor and the lasers (FIG. 3, 18), 17 are preferably visible red semiconductor lasers. The infrared sensor used in this invention was manufactured by Everest Interscience Incorporated and the lasers, each being Part No. LK031, were manufactured by Keyence Inc. The infrared sensor (FIG. 3, 16) and the lasers (FIG. 3, 18), 17 are coupled to the platform 11 and the supporting structure 12 via a coupling means 24 such as clamps, screws, fasteners, or a nut and bolt combination. The coupling means 24 preferably are constructed from aluminum or steel material, however the coupling means 24 may be constructed from any metal, metal alloy, or nonmetal that would provide rigid structural support. The closure feeding pocketwheel, pocketwheel, and closure receiving pocketwheel 13,14,15 are coupled to the platform 11 via coupling means, preferably gears (FIGS. 3 and 4, 26), that are mounted on the closure feeding pocketwheel, pocketwheel, and closure receiving pocketwheel 13,14,15 and are housed below the platform 11. The gears (FIGS. 3 and 4, 26) transfer motion to the pocketwheels 13,14,15 from a motor 19 that is coupled to the gears (FIGS. 3 and 4, 26) and the supporting structure 12. The motor (FIG. 4, 19) is coupled to the gears (FIGS. 3 and 4, 26) and the supporting structure 12 via a coupling means 24 such as clamps, screws, fasteners, or a nut and bolt combination. The coupling means 24 preferably are constructed from aluminum or steel material, however the coupling means 24 may be constructed from any metal, metal alloy, or nonmetal that would provide rigid structural support. For the purposes of this invention, common spur gears were used and the motor 19 is a servomotor. The closure feeding pocketwheel and closure receiving pocketwheel 13,15 move in a direction opposite to the direction the pocketwheel 14 moves. Specifically, the closure feeding pocketwheel and closure receiving pocketwheel 13,15 move in a clockwise direction and the pocketwheel 14 moves in a counterclockwise direction.

Figure 2:
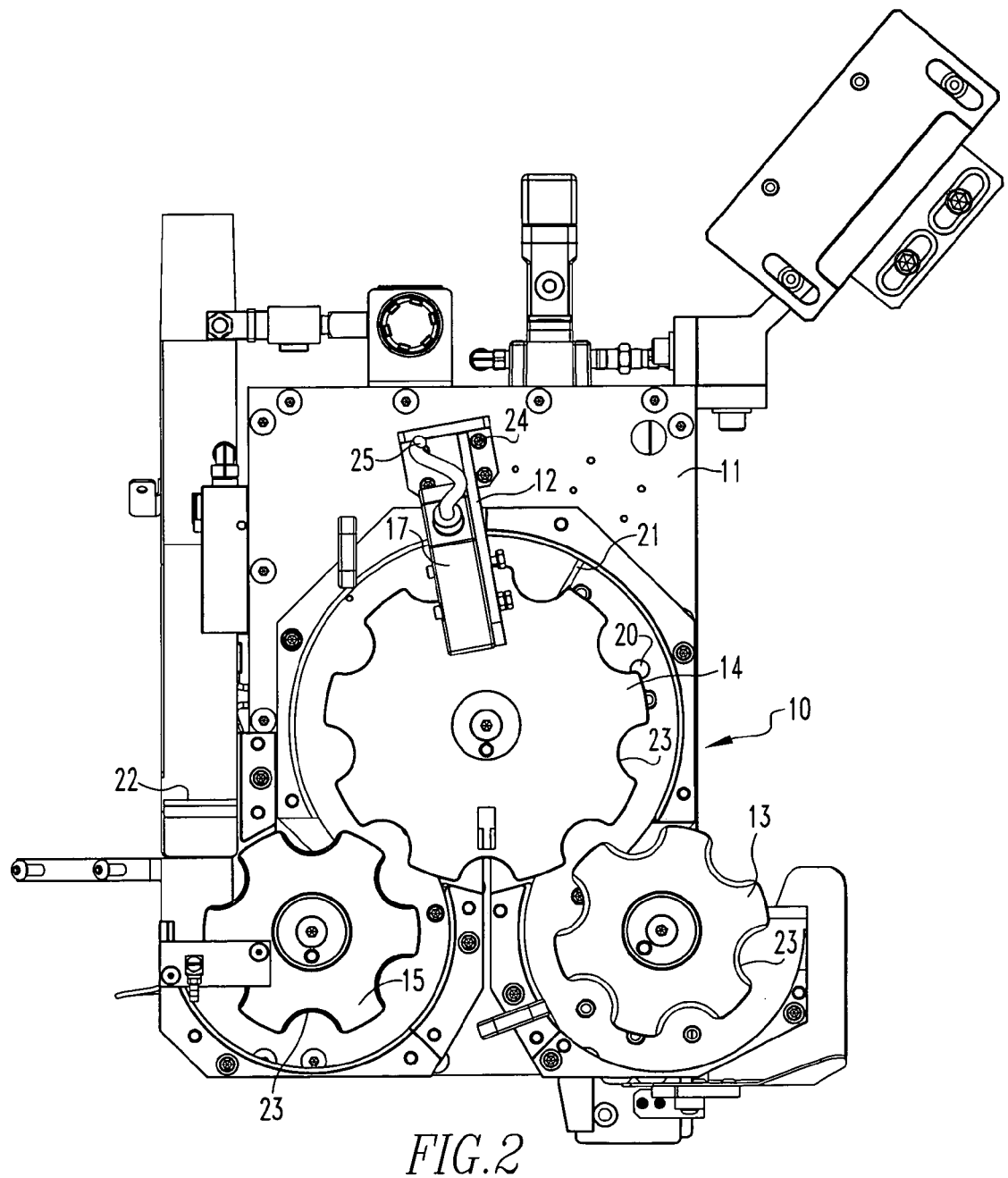
FIG. 2 is a top view of the closure monitor apparatus.

During the monitoring process, the closure feeding pocketwheel 13 accepts a plastic closure, with the plastic closure being upside down, from a molding apparatus that is situated above the monitoring apparatus 10 and beside the closure feeding pocketwheel 13. The closure is then passed from the closure feeding pocketwhel 13 to the pocketwheel 14. The pocketwheel 14 passes the closure above the infrared sensor (FIG. 3, 16) and the first laser (FIG. 3, 18) and below the second laser 17. The infrared sensor (FIG. 3, 16) measures the temperature of the top panel of the closure by emitting an infrared beam onto the top panel and collecting the intensity of the beam reflectance from it. The infrared beam is emitted through an aperture (FIG. 2, 20) on the platform 11 and has a wavelength that is between about 8 to about 14 microns. The aperture (FIG. 2, 20) is about a quarter inch in diameter. The first and second lasers (FIG. 3, 18,), 17 measure the concavity and the location of the inside surface of the top panel respectively by emitting a laser beam onto the outside and inside surfaces of the top panel and collecting the distance from these surfaces to the laser face. For the purposes of this invention, concavity means the maximum depth of the top panel curvature that is observed in the center of the closure top panel. The distance from the outside and inside surfaces of the top panel is measured using the triangulation measurement system. The lasers use a Charged Coupled Device (CCD) array as a light receiving element. The light reflected by the outside and inside surfaces passes through a receiver lens that focuses the light on the CCD. The CCD detects the peak value, or the brightest point, of the light quantity distribution of the laser beam spot and identifies this as the target position on the inside and outside surfaces of the top panel. The thickness of the top panel is then obtained by subtracting the concavity of the top panel from the location of the inside surface of the top panel.

The laser beam from the first laser (FIG. 3, 18) is emitted through a slot (FIG. 2, 21) in the platform 11. Each of the laser beams from the first and second lasers (FIG. 3, 18), 17 have a wavelength that is about 670 nanometers. The slot (FIG. 2, 21) has a width of about one eighth inch and a length of about one inch. The calculation of the measurements can be performed either manually or electronically, but for the purposes of this invention the calculations were performed electronically by a data acquisition control system that is coupled to the infrared sensor (FIG. 3, 16) and lasers (FIG. 3, 18), 17 via electrical wires 25. The control system, which drives the servomotor and synchronizes it to the molding machine rotation, is manufactured from Alan Bradley Programmable Logic Control (PLC) components and proprietary software. After the measurements are performed, the closure is passed from the pocketwheel 14 to the closure receiving pocketwheel 15. Based on the measurements, the closures are either approved or rejected. The closure receiving pocketwheel 15 passes approved closures to a passageway 22 made for collecting the closures. The passageway 22 is coupled to the platform 11, is situated next to the closure receiving pocketwheel 15, and comprises stainless steel. Rejected closures are cleared from the closure receiving pocketwheel 15 and platform 11 by an airway 27 on the side of the platform 11 below the closure receiving pocketwheel 15. The airway 27 comprises an aperture that is about 0.03 inches in diameter and blows the rejected closure into a chute (not shown) that leads the rejected closure into a scrap box (not shown).

Temperature measurement of each closure, by the infrared sensor (FIG. 3, 16), correlates to dimensional shifts, quality shifts, and cooling system performance. Measurement of top panel thickness, by a combination of the measurements of the first and second lasers (FIG. 3,18), 17 correlates directly to closure weight and final dimensions. Warpage indicators or the concavity of the closure top surface, as measured by the first laser (FIG. 3,18), correlates directly to cooling flow and plastic melt temperature. Combinations of measurements' behavior allow technicians to quickly diagnose a problem and point to a sub-system of the molder, or individual tool that requires maintenance or adjustment. Because the measurements are variables, rather than attributes, they lend themselves to control charting, and indicate processes that are changing, thus giving early warning of changing processes and allowing maintenance and adjustment to be performed before scrap is produced. For the purposes of this invention, the process moves at a speed that is equal to the speed of the production flow, which is about 500-600 with the capacity of 1200 parts/minute.

Having described the presently preferred embodiments, it is to be understood that the invention may be otherwise embodied within the scope of the appended claims.

What is claimed is:

1. A method of monitoring molded closures after manufacture of said closures, said method comprising:
    passing said closures above an infrared sensor and measuring the temperature of a top panel of said closure;
    passing said closure above a first laser and measuring the concavity of said top panel;
    passing said closure under a second laser and measuring the location of the inside surface of said top panel;
    obtaining the thickness of said top panel by subtracting said concavity of said top panel from said location of said inside surface of said top panel; and
    approving or rejecting said closure.

2. The method of claim 1 wherein said infrared sensor measures said temperature of said top panel by emitting an infrared beam onto the outside surface of said top panel and collecting the intensity of the beam reflectance from said outside surface.

3. The method of claim 2 wherein said infrared beam has a wavelength that is between about 8 to about 14 microns.

4. The method of claim 1 wherein said first laser and said second laser measures said concavity and said location of said inside surface of said top panel by emitting a laser beam onto said outside and said inside surfaces of said top panel and collecting the distance from said outside and said inside surfaces to said first and said second lasers.

5. The method of claim 4 wherein said laser beam has a wavelength that is about 670 nanometers.

6. The method of claim 1 wherein said approving or rejecting of said closures comprises analyzing of the measurements of said infrared sensor and said first and said second lasers.

7. The method of claim 6 wherein the step of analyzing said measurements of said infrared sensor and said first and said second lasers is performed manually or electronically.

8. The method of claim 7 wherein said step of analyzing said measurements is performed electronically via a data acquisition control system.

9. An apparatus for use in monitoring molded closures after manufacture of said closures, said apparatus comprising:
    a platform having a supporting structure;
    a pocketwheel having pockets for holding said closures;
    a closure feeding means for feeding said closure to said pocketwheel, said closure feeding means radially oriented from said pocketwheel; and
    a closure receiving means for receiving said closure after said closure is discharged from said pocketwheel, said closure receiving means radially oriented from said pocketwheel and across from said closure feeding means,
    wherein said pocketwheel, said closure feeding means, and said closure receiving means are coupled to said platform via a coupling means mounted on said pocketwheel, said closure feeding means, and said closure receiving means, said coupling means transferring motion to said pocketwheel, said closure feeding means, and said closure receiving means from a motor coupled to said coupling means;
    an infrared sensor coupled to said platform;
    a first laser positioned below said platform and coupled to said supporting structure; and
    a second laser positioned above said platform and coupled to said supporting structure.

10. The apparatus of claim 9 wherein said closure feeding means accepts said closure from a molding apparatus and passes said closure to said pocketwheel, said pocketwheel passes said closure above said infrared sensor and said first laser and below said second laser, said infrared sensor and said lasers each measuring a parameter of said closure for approval or rejection of said closure, said pocketwheel passes closures to said closure receiving means, said closure receiving means clearing said approved closures from said platform, said rejected closures cleared from said platform.

11. The apparatus of claim 10 wherein said rejected closures are cleared from said platform via an airway on the side of said platform.

12. The apparatus of claim 11 wherein said airway comprises an aperture having a diameter of about 0.030 inches.

13. The apparatus of claim 9 wherein said closure feeding means and said closure receiving means each comprise a pocketwheel having pockets for holding said closures.

14. The apparatus of claim 13 wherein the diameter of said pockets of said closure feeding means and said closure receiving means is about 30 mm.

15. The apparatus of claim 9 wherein said coupling means comprises gears.

16. The apparatus of claim 9 wherein said platform includes an aperture to receive an infrared beam from said infrared sensor and a slot to receive a laser beam from said first laser.

17. The apparatus of claim 16 wherein the diameter of said aperture is about a quarter inch and the width and the length of said slot is about an eighth inch and about one inch.

18. The apparatus of claim 9 wherein the diameter of said closure feeding means and said closure receiving means is about 4.5 inches.

19. The apparatus of claim 9 wherein the diameter of said pocketwheel is about 7 inches.

20. The apparatus of claim 9 wherein the diameter of said pockets of said pocketwheel is about 30 mm.

21. The apparatus of claim 9 wherein said closure feeding means comprises plastic.

22. The apparatus of claim 21 wherein said plastic comprises high density polyethylene.

23. The apparatus of claim 9 wherein said pocketwheel and said closure receiving means comprise metal.

24. The apparatus of claim 23 wherein said metal comprises coated aluminum.

25. The apparatus of claim 9 wherein said infrared sensor measures the temperature of the top panel of said closure by emitting an infrared beam onto the outside surface of said top panel and collecting the intensity of the beam reflectance from said outside surface.

26. The apparatus of claim 25 wherein said infrared beam has a wavelength of between about 8 to about 14 microns.

27. The apparatus of claim 9 wherein said first laser and said second laser measure the concavity and the location of the inside surface of said top panel of said closure by emitting a laser beam onto said outside and said inside surfaces of said top panel and collecting the distance from said outside and said inside surfaces to said first and said second lasers.

28. The apparatus of claim 27 wherein said laser beam has a wavelength that is about 670 nanometers.

* * * * *